(12) United States Patent
Arnin (10) Patent No.: US 11,547,450 B2
(45) Date of Patent: Jan. 10, 2023

(54) EXPANDABLE POLYAXIAL SPINAL SYSTEM

(71) Applicant: ApiFix, Ltd, Carmiel (IL)

(72) Inventor: Uri Arnin, Kiryat Tivon (IL)

(73) Assignee: ApiFix Ltd.

( * ) Notice: Subject to any disclaimer, the term of this patent is extended or adjusted under 35 U.S.C. 154(b) by 0 days.

(21) Appl. No.: 16/429,198

(22) Filed: Jun. 3, 2019

(65) Prior Publication Data

US 2019/0282277 A1 Sep. 19, 2019
US 2020/0375629 A9 Dec. 3, 2020

Related U.S. Application Data

(63) Continuation-in-part of application No. 15/564,199, filed as application No. PCT/IB2016/052075 on Apr. 12, 2016, now abandoned.

(60) Provisional application No. 62/178,691, filed on Apr. 17, 2015.

(51) Int. Cl.
  *A61B 17/70* (2006.01)
  *A61B 17/68* (2006.01)

(52) U.S. Cl.
  CPC ...... *A61B 17/7014* (2013.01); *A61B 17/7001* (2013.01); *A61B 17/7007* (2013.01); *A61B 17/7017* (2013.01); *A61B 2017/681* (2013.01)

(58) Field of Classification Search
  CPC ............ A61B 17/7014; A61B 17/7001; A61B 17/7007; A61B 17/7017; A61B 17/7023; A61B 17/7025; A61B 17/7028; A61B 2017/681
  USPC ........................ 606/256–260, 265, 266, 278
  See application file for complete search history.

(56) References Cited

U.S. PATENT DOCUMENTS

| 5,413,602 | A | * | 5/1995 | Metz-Stavenhagen ...................... A61B 17/7014 606/247 |
| 5,468,241 | A | | 11/1995 | Metz-Stavenhagen et al. |
| 5,540,688 | A | | 7/1996 | Navas |
| 6,241,730 | B1 | | 6/2001 | Alby |
| 6,264,658 | B1 | | 7/2001 | Lee et al. |
| 7,029,475 | B2 | * | 4/2006 | Panjabi .............. A61B 17/7007 606/279 |
| 7,611,526 | B2 | | 11/2009 | Carl et al. |
| 7,935,134 | B2 | * | 5/2011 | Reglos ............... A61B 17/7037 606/257 |
| 8,025,681 | B2 | | 9/2011 | Colleran |
| 8,475,498 | B2 | * | 7/2013 | Jackson ............. A61B 17/7026 606/254 |

(Continued)

FOREIGN PATENT DOCUMENTS

| JP | H78504 | 1/1995 |
| JP | 200033091 | 2/2000 |

(Continued)

OTHER PUBLICATIONS

PCT Search Report PCT/IB2016/052075, dated Sep. 7, 2016.

(Continued)

*Primary Examiner* — Eduardo C Robert
*Assistant Examiner* — David C Comstock
(74) *Attorney, Agent, or Firm* — Gerald W. Roberts; John V. Daniluck; Dentons Bingham Greenebaum LLP (57) ABSTRACT

A spinal pedicle screw system includes distractions rods and has the ability to be distracted after the screws are inserted into the pedicle and maintain polyaxial motion via polyaxial joints.

8 Claims, 6 Drawing Sheets

(56) References Cited

U.S. PATENT DOCUMENTS

| | | | |
|---|---|---|---|
| 8,475,499 B2 | 7/2013 | Cournoyer | |
| 8,777,995 B2* | 7/2014 | McClintock | A61B 17/7041 606/258 |
| 8,828,058 B2* | 9/2014 | Elsebaie | A61B 17/705 606/258 |
| 8,926,669 B2 | 1/2015 | Jacofsky et al. | |
| 8,992,576 B2 | 3/2015 | Keyer et al. | |
| 9,023,087 B2 | 5/2015 | Frankel et al. | |
| 9,517,089 B1 | 12/2016 | NuVasive | |
| 2003/0009226 A1 | 1/2003 | Graf | |
| 2003/0055427 A1* | 3/2003 | Graf | A61B 17/7025 623/17.12 |
| 2005/0182401 A1 | 8/2005 | Timm | |
| 2005/0228382 A1 | 10/2005 | Richelsoph et al. | |
| 2008/0195100 A1 | 8/2008 | Capote et al. | |
| 2008/0234743 A1 | 9/2008 | Marik | |
| 2009/0093820 A1* | 4/2009 | Trieu | A61B 17/701 606/264 |
| 2009/0306717 A1* | 12/2009 | Kercher | A61B 17/7017 606/258 |
| 2010/0249836 A1* | 9/2010 | Seme | A61B 17/7035 606/246 |
| 2011/0307015 A1* | 12/2011 | Zucherman | A61B 17/7007 606/264 |
| 2012/0130430 A1 | 5/2012 | Le Roux | |
| 2013/0018421 A1 | 1/2013 | George | |
| 2014/0296918 A1* | 10/2014 | Fening | A61B 17/7016 606/258 |
| 2015/0335358 A1 | 11/2015 | Luhmann | |
| 2016/0106471 A1 | 4/2016 | Lynch | |
| 2018/0125533 A1 | 5/2018 | Arnin | |
| 2019/0059950 A1 | 2/2019 | Di Lauro et al. | |

FOREIGN PATENT DOCUMENTS

| | | |
|---|---|---|
| JP | 2003518978 | 6/2003 |
| JP | 2008504070 | 2/2008 |
| JP | 5305101 | 1/2011 |
| WO | 2004/075778 | 9/2004 |
| WO | 2006002333 | 1/2006 |

OTHER PUBLICATIONS

JP 2017553116, Notice of Reasons for Refusal, 5 pages, Apr. 5, 2021.
PCT/IB2020/000423, International Search Report and Written Opinion, 9 pages, dated Oct. 19, 2020.
USPTO, Ex. Lee Young, Search Report and Written Opinion, 8 pgs. Oct. 19, 2020.
U.S. Appl. No. 15/564,199, Nonfinal Office Action, 6 pgs, dated Jun. 1, 2018.
U.S. Appl. No. 15/564,199, Applicant Response, 5 pages, dated Sep. 3, 2018.
U.S. Appl. No. 15/564,199, Final Rejection, 6 pgs, dated Jan. 8, 2019.
PCT/IB2016/052075, ISA/EPO, International Search Report and Written Opinion, 8 pgs, dated Jul. 9, 2016.
BR112017022208-6, Preliminary Office Action, 5 pgs, dated May 19, 2020.
BR112017022208-6, Response Filed, 8 pgs, dated Aug. 17, 2020.
CN 201680022348.80, Notification of the Second Office action, 9 pgs, dated Apr. 15, 2020.
CN 201680022348.80, Response to Second Office Action, 16 pgs. dated Aug. 28, 2020.
CN 201680022348.80, Third Office Action, 8 pgs. dated Dec. 14, 2020.
CN 201680022348.80, Response to Third Office Action, 5 pgs, dated Feb. 25, 2021.
JP 2017553116, Notice of Reasons for Refusal, 4 pgs, dated May 11, 2020.
JP 2017553116, Response filed, 7 pgs (Englsh translation of claims only) dated Nov. 17, 2020.
PCT/IB2020/000423, ISA/US, Search Report and Written Opinion, 7 pgs, dated Oct. 19, 2020.

* cited by examiner

EXPANDABLE POLYAXIAL SPINAL SYSTEM

FIELD OF THE INVENTION

The present invention relates generally to spinal implants and prostheses, and particularly to a spinal pedicle screws based system designed to be expandable and maintain polyaxial motion in situ.

BACKGROUND OF THE INVENTION

Spine scoliosis is affecting significant portion of the population. Current surgical treatment involves many times the use of an intervertebral pedicle screws based systems designed to be placed between two or more vertebrae.

The use of standard pedicle screws system is typically associated with spinal fusion, which has some known negative impacts. It is of value therefor to have a non-fusion system that can prevent or correct scoliosis of some patients.

SUMMARY OF THE INVENTION

The present invention seeks to provide an improved spinal pedicle screws based system that can be expanded after the screws are inserted to the pedicles of the two vertebrae and maintain spinal motion via one or more polyaxial joints.

There is thus provided in accordance with a non-limiting embodiment of the present invention a spinal system including a first distraction rod which has a first connector mounted at an end thereof, and a second distraction rod which has a second connector mounted at an end thereof, both of the rods being arranged to move in a housing, and wherein each of the connectors is mounted on a polyaxial joint and secured by a fastener, each of the polyaxial joints being attached to, or part of, a pedicle screw, and wherein the fastener is tightened against a portion of the polyaxial joint but does not inhibit polyaxial movement of the polyaxial joint, such that even after tightening the fastener, the connectors cannot move off the polyaxial joints but the polyaxial joints are free to move polyaxially at all times.

In accordance with an embodiment of the present invention at least one of the first and second distraction rods is affixed by a distraction fastener at any desired location along the housing.

In accordance with an embodiment of the present invention at least one of the first and second distraction rods is rotated about its longitudinal axis before being locked in place by the distraction fastener.

In accordance with an embodiment of the present invention at least one of the distraction rods is at least partially threaded and mates with an internal thread in the housing.

In accordance with an embodiment of the present invention both of the distraction rods are at least partially threaded and mate with an internal thread in the housing, and wherein threads of one of the distraction rods are right-handed and threads of the other distraction rod are left-handed.

In accordance with an embodiment of the present invention the housing includes a fluid inlet for introducing therethrough fluid.

In accordance with an embodiment of the present invention the housing includes a biasing device operative to apply a biasing force on at least one of the first and second distraction rods.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
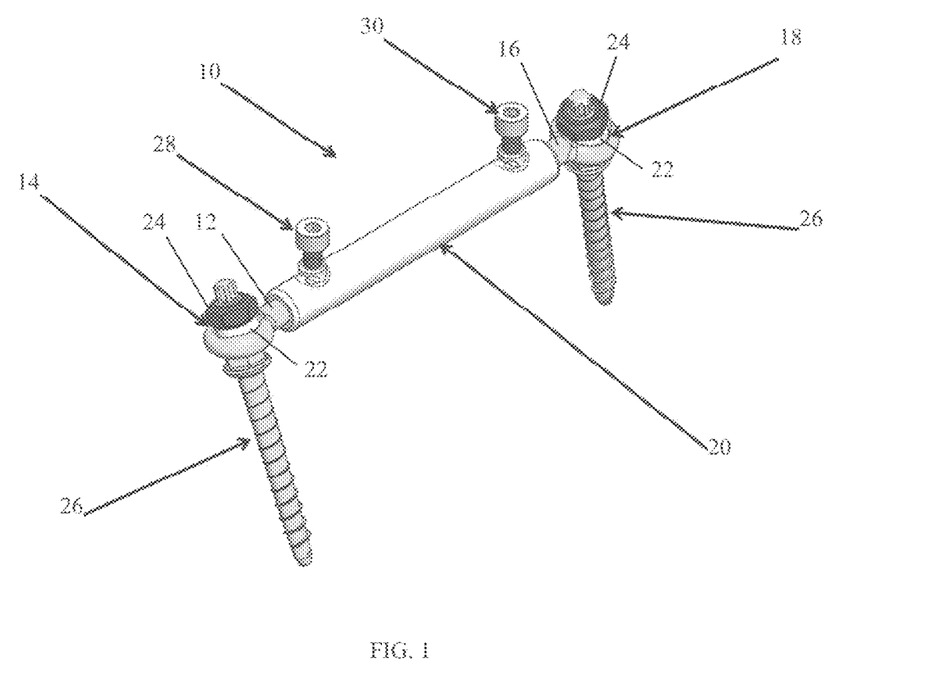
FIG. 1 is a simplified pictorial illustration of a spinal system, in an initial contracted configuration before distraction, constructed and operative in accordance with a non-limiting embodiment of the invention.
Figure 2:
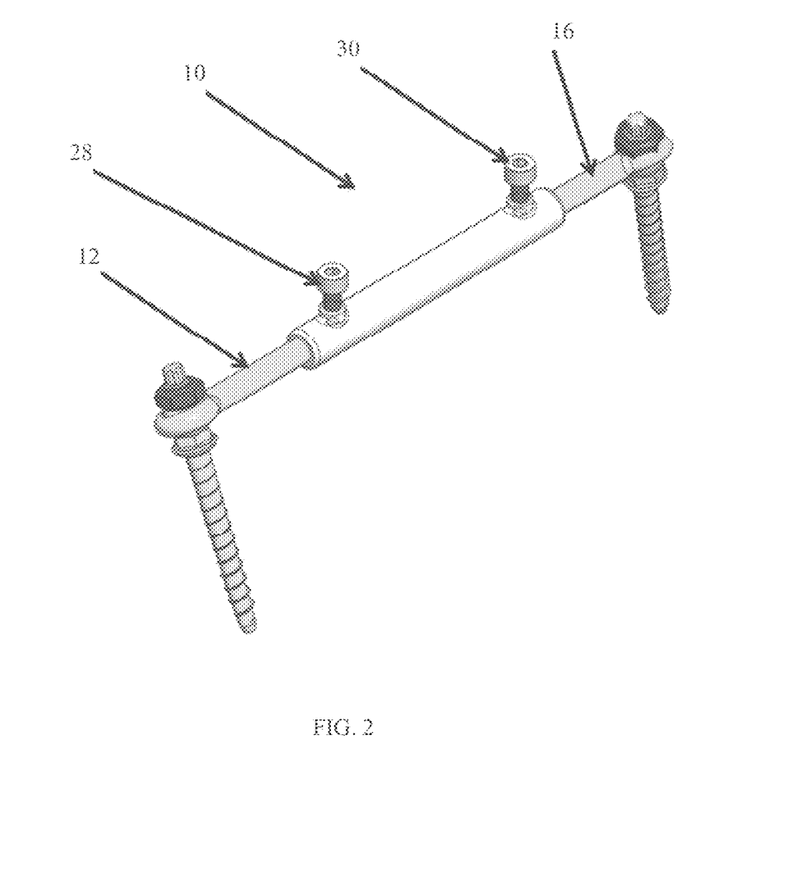
FIG. 2 is a simplified pictorial illustration of the spinal system in an expanded/distracted configuration.
Figure 3:
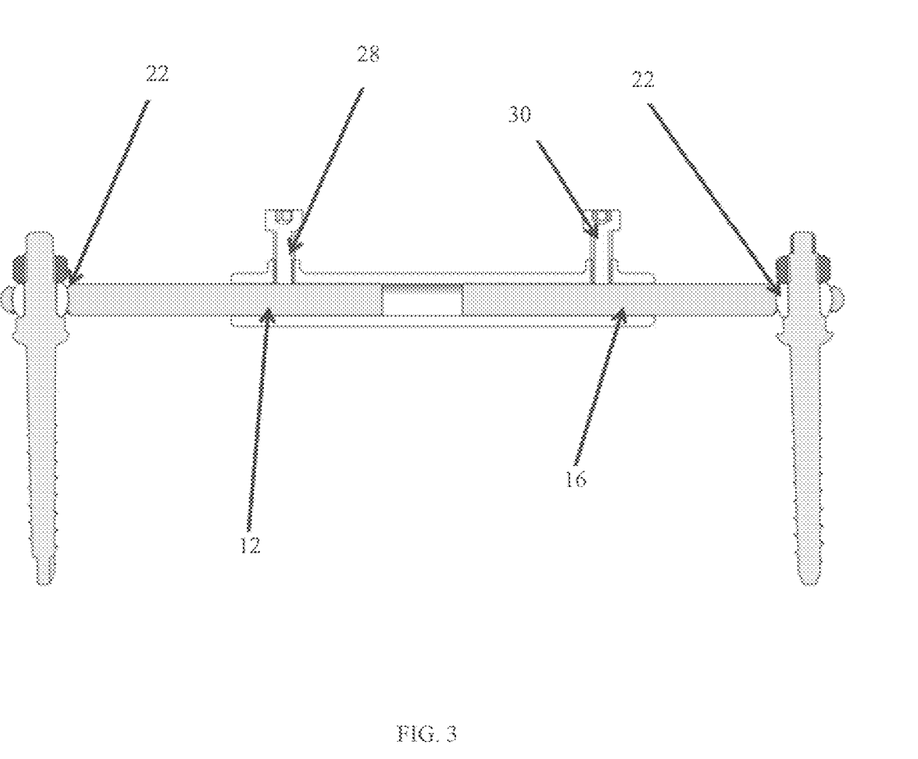
FIG. 3 is a simplified, cutaway illustration of the system in its expanded/distracted configuration.

Reference is now made to FIGS. 1-3, which illustrate a spinal system 100, constructed and operative in accordance with a non-limiting embodiment of the invention.

The spinal system 10 includes a first distraction rod 12 which has a first connector 14 mounted at an end thereof, and a second distraction rod 16 which has a second connector 18 mounted at an end thereof. Both rods 12 and 16 are arranged to move (e.g., translate or slide) in a housing 20. Both connectors 14 and 18 may each include a ring mounted on a polyaxial joint 22 (which may be, without limitation, a spherically shaped head) and secured by a fastener 24, such as a nut. The polyaxial joint 22 may be attached to, or may be part of, a pedicle screw 26. The fastener 24 is tightened against a portion (in the illustration, the upper portion) of the polyaxial joint 22 but does not inhibit polyaxial movement of the polyaxial joint. Thus, even after tightening the fastener 24, the connector 14 or 18 cannot move off the polyaxial joint but the polyaxial joint is free to move polyaxially at all times.

Distraction fasteners 28 and 30 may fasten the first and second distraction rods 12 and 16, respectively, at any desired location along housing 20.

After inserting the pedicle screws 26 into the patient's vertebrae it is possible to distract or expand (the terms being used interchangeably) the distance between the screws by using a distractor (not shown) or any other suitable means. The distracted orientation is shown in FIG. 2. After distraction the distraction fasteners 28 and 30 can be used to fix the distance between the pedicle screws.

As seen in FIGS. 1 and 2, the first and second distraction rods 12 and 16 may be rotated about their respective longitudinal axes before being locked in place by distraction fasteners 28 and 30. For example, only one of the distraction rods may be rotated while the other is not rotated, or both may be rotated. As another example, only one of the distraction rods may be distracted while the other is not distracted, or both may be distracted. Whichever rods is not distracted may be locked in place by the distraction fastener, or alternatively, may be left unlocked, in which case that rod is free to move in translation and in rotation.

Figure 4:
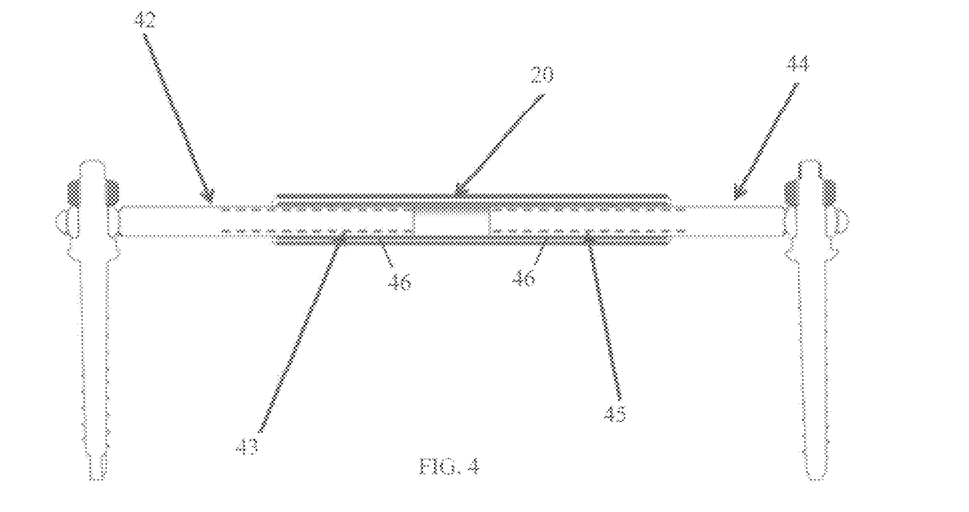
FIG. 4 is a simplified pictorial illustration of a spinal system, constructed and operative in accordance with another non-limiting embodiment of the invention, wherein distraction is done using threaded elements.

Reference is now made to FIG. 4, which illustrates a spinal system, constructed and operative in accordance with another non-limiting embodiment of the invention, with like elements being designated by like numerals. In this embodiment, distraction rods 42 and 44 are at least partially threaded and mate with an internal thread 46 in housing 20. Distraction may be done by rotating the rods with respect to the housing, that is, by rotating the rods with the housing stationary or by rotating the housing with the rods not rotating, or by rotating both the rods and the housing. In one embodiment, threads 43 of rod 42 are right-hand threads whereas threads 45 of rod 44 are left-hand threads. In this manner, rotating the housing in one direction causes the rods 42 and 44 to move simultaneously in opposite directions. After distraction to the desired distance between the pedicle screws, distraction fasteners (not shown) may be used to fix the system at the desired position.

Figure 4A:
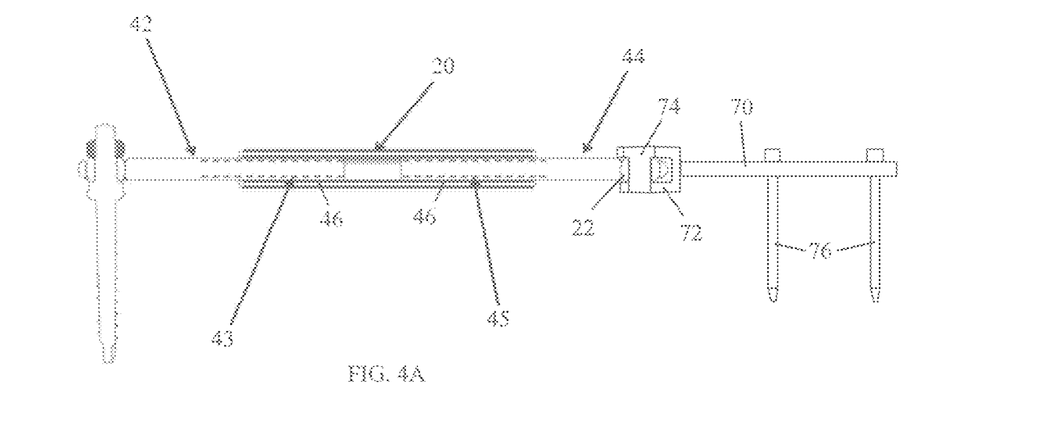
FIG. 4A is a simplified pictorial illustration of a spinal system, constructed and operative in accordance with another non-limiting embodiment of the invention, including an extender member which may be fixedly or pivotally attached to the spinal system.

Reference is now made to FIG. 4A, which illustrates another version of the spinal system of FIG. 4. It is noted that the embodiment of FIG. 4A can also be implemented with any of the other embodiments and is not limited to distraction rods that are in threaded engagement with the housing.

In the version of FIG. 4A, an extender member 70 is a rod coupled to a connecting element 72, which may be U-shaped. Connecting element 72 may be coupled to the polyaxial joint 22 of the distraction rod 44 by a fastener 74, such as a screw. As described above for fastener 24, here too, fastener 74 is tightened against a portion of the polyaxial joint 22 but does not inhibit polyaxial movement of the polyaxial joint 22. Thus, even after tightening the fastener 74, the extender member 70 cannot move off the polyaxial joint 22 but the polyaxial joint 22 is free to move polyaxially at all times. Thus, there is free polyaxial movement between the extender member 70 and distraction rod 44.

The extender member 70 may be secured to spinal structure with one or two pedicle screws 76. The extender member 70 may be collinear with rod 44 or may be tilted with respect to rod 44.

Figure 5:
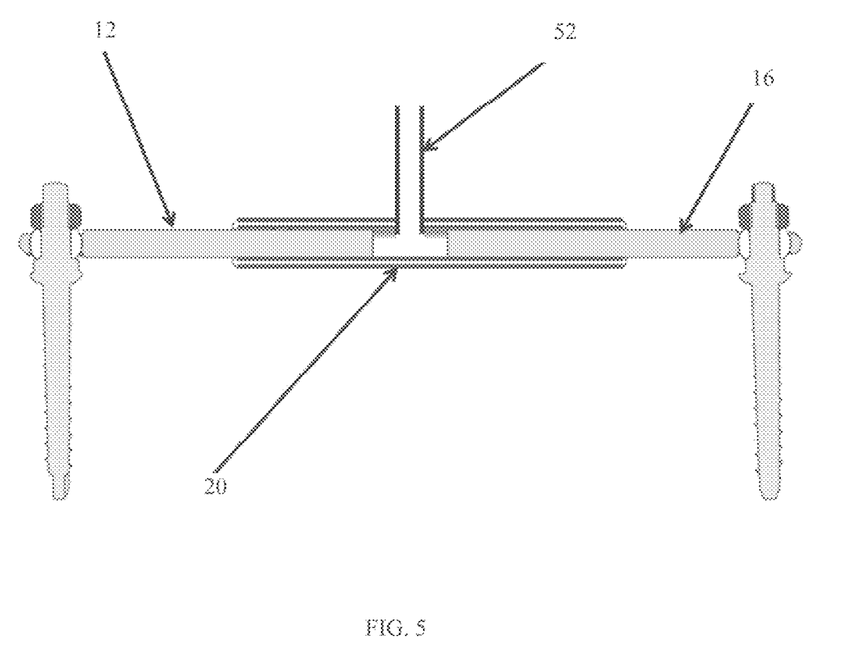
FIG. 5 is a simplified pictorial illustration of a spinal system, constructed and operative in accordance with another non-limiting embodiment of the invention, wherein distraction is done using hydraulic or pneumatic force.

Reference is now made to FIG. 5, which illustrates a spinal system, constructed and operative in accordance with another non-limiting embodiment of the invention, with like elements being designated by like numerals. In this embodiment, distraction is done using hydraulic or pneumatic force. For example, housing 20 may be provided with a fluid inlet 52 for introducing therethrough fluid (e.g., water, saline, air, etc.). The fluid pressure acts on rods 12 and 16 and increase the distance between them. Sealing rings (not shown) may be provided to seal the fluid in the housing 20. The fluid may be introduced at any point during or after the surgical procedure.

In one embodiment, one of the rods can be affixed to the housing while the other rod is distracted by the fluid (hydraulic or pneumatic) force.

Figure 6:
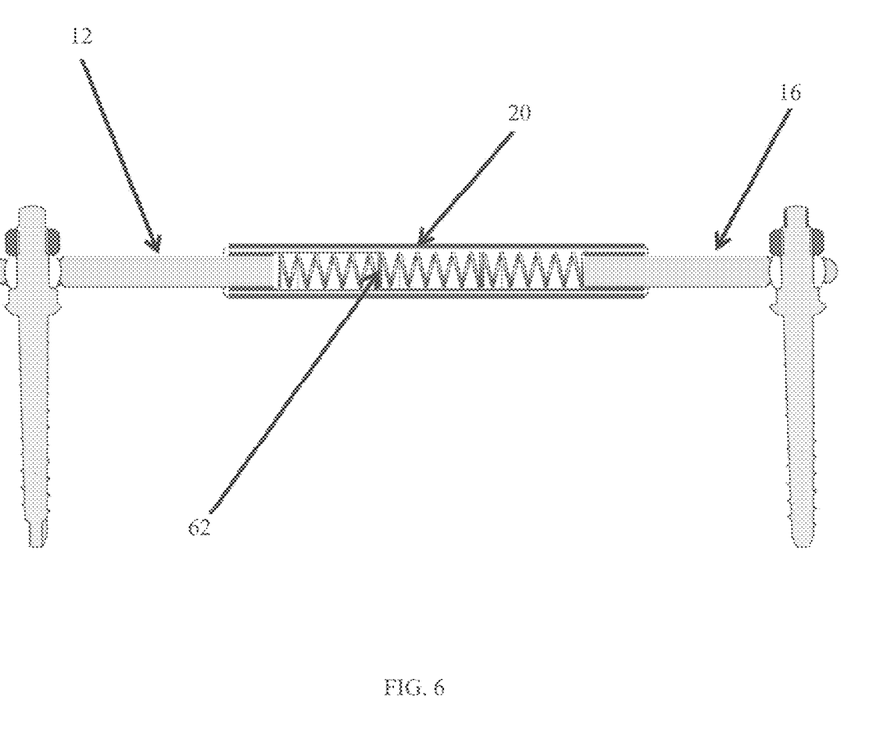
FIG. 6 is a simplified pictorial illustration of a spinal system, constructed and operative in accordance with another non-limiting embodiment of the invention, wherein distraction is done using a biasing device.

Reference is now made to FIG. 6, which illustrates a spinal system, constructed and operative in accordance with another non-limiting embodiment of the invention, with like elements being designated by like numerals. In this embodiment, distraction is done using a biasing device 62 disposed in the housing, such as a coil spring or flexible band. Biasing device 62 may be made of metal or elastomeric materials. Biasing device 62 may apply a constant or variable spring force on the rods 12 and 16.

In one embodiment, one of the rods can be affixed to the housing while the other rod is distracted by the spring force.

What is claimed is:

1. A spinal system, comprising:
a first distraction rod which has a first connector mounted at an end thereof;
a housing;
a second distraction rod which has a second connector mounted at an end thereof; and
a pair of distraction fasteners,
wherein each of said distraction rods is arranged to rotate within said housing,
wherein each of said distraction rods is arranged to translate linearly within said housing independently of rotating within said housing,
wherein each of said connectors is mounted on a respective one of a pair of polyaxial joints and secured by one of a respective pair of fasteners,
wherein each of said polyaxial joints is attached to a respective one of a pair of pedicle screws,
wherein when said fasteners are tightened against respective portions of said polyaxial joints said connectors are not free to move off said polyaxial joints and said polyaxial joints are free to operate polyaxially,
wherein at least one of said first and second distraction rods is arranged to be affixed, by one of said distraction fasteners, at any desired linear translation within said housing,
wherein at least one of said first and second distraction rods is arranged to be affixed, by one of said distraction fasteners, at any desired rotational position within said housing, and
wherein said housing comprises a fluid inlet for introducing therethrough fluid to separate said distraction rods.

2. A spinal system, comprising:
a first distraction rod which has a first connector mounted at an end thereof;
a housing;
a second distraction rod which has a second connector mounted at an end thereof; and
a pair of distraction fasteners,
wherein each of said distraction rods is arranged to rotate within said housing,
wherein each of said distraction rods is arranged to translate linearly within said housing independently of rotating within said housing,
wherein each of said connectors is mounted on a respective one of a pair of polyaxial joints and secured by one of a respective pair of fasteners,
wherein each of said polyaxial joints is part of a respective one of a pair of pedicle screws,
wherein when said fasteners are tightened against respective portions of said polyaxial joints said connectors are not free to move off said polyaxial joints and said polyaxial joints are free to operate polyaxially,
wherein at least one of said first and second distraction rods is arranged to be affixed, by one of said distraction fasteners, at any desired linear translation within said housing,
wherein at least one of said first and second distraction rods is arranged to be affixed, by one of said distraction fasteners, at any desired rotational position within said housing, and
wherein said housing comprises a fluid inlet for introducing therethrough fluid to separate said distraction rods.

3. A spinal system, comprising:
a first pedicle screw;
a first polyaxial joint attached to said first pedicle screw;
a first distraction rod having a first connector mounted on said first polyaxial joint at an end of said first distraction rod;
a first fastener securing said first connector to said first polyaxial joint;
a second polyaxial joint;
a second distraction rod having a second connector mounted on said second polyaxial joint at an end of said second distraction rod;
an extender member;
a connecting element coupled to said extender member;
an extender member fastener securing said connecting element to said second polyaxial joint;
a housing; and
a pair of distraction fasteners,
wherein each of said distraction rods is arranged to rotate within said housing,
wherein each of said distraction rods is arranged to translate linearly within said housing independently of rotating within said housing,
wherein when said first fastener is tightened against a portion of said first polyaxial joint said first connector is not free to move off said first polyaxial joint and said first polyaxial joint is free to operate polyaxially,
wherein when said extender member fastener is tightened against a portion of said second polyaxial joint said connecting element is not free to move off said second polyaxial joint, said second polyaxial joint is free to operate polyaxially, said extender member is free to move polyaxially relative to said second distraction rod, and said extender member is not free to translate linearly relative to said second distraction rod,
wherein said extender member is freely longitudinally alignable along a radius of a range of solid angles apexed at said second polyaxial joint, wherein said extender member is arranged to be free to become collinear with said second distraction rod,
wherein at least one of said first and second distraction rods is arranged to be affixed, by one of said distraction fasteners, at any desired linear translation within said housing,
wherein at least one of said first and second distraction rods is arranged to be affixed, by one of said distraction fasteners, at any desired rotational position within said housing, and
wherein said housing comprises a fluid inlet for introducing therethrough fluid to separate said distraction rods.

4. The spinal system according to claim 3, wherein said extender member is configured to receive a plurality of pedicle screws therethrough.

5. The spinal system according to claim 4, wherein said extender member is an extender rod.

6. A spinal system, comprising:
a first pedicle screw comprising a first polyaxial joint;
a first distraction rod having a first connector mounted on said first polyaxial joint at an end of said first distraction rod;
a first fastener securing said first connector to said first polyaxial joint;
a second polyaxial joint;
a second distraction rod having a second connector mounted on said second polyaxial joint at an end of said second distraction rod;
an extender member;
a connecting element coupled to said extender member;
an extender member fastener securing said connecting element to said second polyaxial joint;
a housing; and
a pair of distraction fasteners,
wherein each of said distraction rods is arranged to rotate within said housing,
wherein each of said distraction rods is arranged to translate linearly within said housing independently of rotating within said housing,
wherein when said first fastener is tightened against a portion of said first polyaxial joint said first connector is not free to move off said first polyaxial joint and said first polyaxial joint is free to operate polyaxially,
wherein when said extender member fastener is tightened against a portion of said second polyaxial joint said connecting element is not free to move off said second polyaxial joint, said second polyaxial joint is free to operate polyaxially, said extender member is free to move polyaxially relative to said second distraction rod, and said extender member is not free to translate linearly relative to said second distraction rod,
wherein said extender member is freely longitudinally alignable along a radius of a range of solid angles apexed at said second polyaxial joint, wherein said extender member is arranged to be free to become collinear with said second distraction rod,
wherein at least one of said first and second distraction rods is arranged to be affixed, by one of said distraction fasteners, at any desired linear translation within said housing,
wherein at least one of said first and second distraction rods is arranged to be affixed, by one of said distraction fasteners, at any desired rotational position within said housing, and
wherein said housing comprises a fluid inlet for introducing therethrough fluid to separate said distraction rods.

7. The spinal system according to claim 6, wherein said extender member is configured to receive a plurality of pedicle screws therethrough.

8. The spinal system according to claim 7, wherein said extender member is an extender rod.

* * * * *